United States Patent
Moss et al.

(10) Patent No.: US 10,359,382 B2
(45) Date of Patent: Jul. 23, 2019

(54) SYSTEM METHOD AND APPARATUS FOR HUMIDITY SENSOR TEMPERATURE COMPENSATION

(71) Applicant: Dwyer Instruments, Inc., Michigan City, IN (US)

(72) Inventors: Robert Austin Moss, Saint Joseph, MI (US); Neal Warren Syverson, Rolling Prairie, IN (US); Daniel A. Heuer, New Carlisle, IN (US); Larry R. Roth, Chesterton, IN (US)

(73) Assignee: DWYER INSTRUMENTS, INC., Michigan City, IN (US)

( * ) Notice: Subject to any disclaimer, the term of this patent is extended or adjusted under 35 U.S.C. 154(b) by 559 days.

(21) Appl. No.: 14/247,428

(22) Filed: Apr. 8, 2014

(65) Prior Publication Data

US 2015/0285755 A1 Oct. 8, 2015

(51) Int. Cl.
| | |
|---|---|
| *G01N 19/10* | (2006.01) |
| *G01N 27/04* | (2006.01) |
| *G01N 27/12* | (2006.01) |
| *G01N 27/22* | (2006.01) |

(52) U.S. Cl.
CPC ............ *G01N 27/121* (2013.01); *G01N 19/10* (2013.01); *G01N 27/046* (2013.01); *G01N 27/223* (2013.01)

(58) Field of Classification Search
CPC .................................................. G01N 27/121
See application file for complete search history.

(56) References Cited

U.S. PATENT DOCUMENTS

| | | | |
|---|---|---|---|
| 3,691,457 | A | 9/1972 | Kriellaars |
| 4,107,599 | A | 8/1978 | Preikschat |
| 5,430,384 | A | 7/1995 | Hocker |
| 5,792,938 | A | 8/1998 | Gokhfeld |
| 6,073,480 | A | 6/2000 | Gokhfeld |
| 6,250,134 | B1 | 6/2001 | Ruppert |
| 6,990,847 | B2 | 1/2006 | Happach |
| 7,077,004 | B2 | 7/2006 | Mitter |

(Continued)

OTHER PUBLICATIONS

Lulea University of Technology, "Moise Air (Psychrometry), Energy Management Handbook", 2007, 19 pages.

(Continued)

*Primary Examiner* — Manuel A Rivera Vargas
(74) *Attorney, Agent, or Firm* — Tarolli, Sundheim, Covell & Tummino LLP

(57) ABSTRACT

A humidity sensor arrangement for providing temperature compensated measurements. A first sensor is configured internal to a housing for the sensor arrangement, and a second sensor is configured external to the housing. The first sensor measures a first relative humidity at a first temperature, and the second sensor measures second temperature external. A processor determines saturation pressures for the first and second sensors and compensates the first sensor by adjusting the relative humidity for the first sensor to be a product of the relative humidity for the first sensor and a ratio of the saturation pressure of the first and second sensors. Further compensation may be produced by applying a time-based filter algorithm to the outputs of the first and second sensors. Temperature sensors can be compensated to determine room temperature and compensated temp can be used for precise humidity compensation.

14 Claims, 4 Drawing Sheets

(56) References Cited

U.S. PATENT DOCUMENTS

| | | |
|---|---|---|
| 7,509,838 B2 | 3/2009 | Paukkunen |
| 8,175,835 B2 | 5/2012 | Dmytriw et al. |
| 8,348,500 B2 | 1/2013 | Sakami |
| 8,359,906 B2 | 1/2013 | Shimada et al. |
| 2003/0051023 A1* | 3/2003 | Reichel .............. G01N 33/0075 709/223 |
| 2005/0188747 A1* | 9/2005 | Kellerman ............ G01N 25/56 73/29.01 |

OTHER PUBLICATIONS

European Search Report to corresponding European Pat. Appl. No. 15159690.5, dated Aug. 20, 2015, 7 pages.
Canadian Office Action to corresponding Canadian Pat. Appl. No. 2,887,288, dated May 18, 2016, 5 pages.

* cited by examiner

SYSTEM METHOD AND APPARATUS FOR HUMIDITY SENSOR TEMPERATURE COMPENSATION

TECHNICAL FIELD

The present disclosure is directed to temperature and/or humidity sensors. More specifically, the present disclosure is directed to temperature compensation for temperature and/or humidity sensors configured for building automation systems (BAS) applications.

BACKGROUND INFORMATION

The demand for multi-variable sensors for the BAS market is increasing steadily, Sensors used for this purpose are generally wall mounted in the zone of a building and comprise one or more sensors, such as temperature, humidity, carbon dioxide ($CO_2$) and volatile organic compounds (VOCs). Additionally, sensors may require the ability to communicate over a wired or wireless communication network. The combination of these sensing abilities and electronics requires more power and therefore results in additional heat being generated in the wall mount case that contains the sensors.

Certain sensors, such as humidity sensors, may be particularly sensitive to temperature differences and gradients surrounding the sensor. When temperatures are artificially increased in the wall mount case, this in turn elevates the temperature of the internal humidity sensor, and may cause errors relative to the humidity in the room. While electrical and thermal design can minimize the increase in heat, there is a need to compensate the humidity sensor inside the wall mount case to match the actual humidity in the room containing the wall mount case.

SUMMARY

Accordingly, under one exemplary embodiment, a temperature-compensated humidity sensor arrangement is disclosed, comprising a first sensor, arranged internal to a housing for the sensor arrangement, wherein the first sensor is configured to determine a first relative humidity at a first temperature internal to the housing. The sensor arrangement further includes a second sensor, arranged external to the housing, wherein the second sensor is configured to determine a second temperature external to the housing. A processor is operatively coupled to the first and second sensor, wherein the processor is configured to compensate the first sensor, based on a function of the second temperature.

In another exemplary embodiment, the first sensor of the sensor arrangement is configured to determine a first relative humidity at a first temperature along multiple points of a time base, and the second sensor is configured to determine a second temperature along the multiple points of the time base. The processor may be configured to apply a time-based filter for the multiple points of the time base. The time-based filter may be applied sequentially or symmetrically for the multiple points of the time base.

In another exemplary embodiment, a method is disclosed for temperature compensated humidity sensing for a sensor arrangement, comprising the steps of determining a first relative humidity at a first temperature internal to a housing for the sensor arrangement via a first sensor; determining a second temperature external to the housing via a second sensor; and compensating the first sensor based on a function of the second temperature.

In another exemplary embodiment, the method includes the step of determining a first saturation pressure for the first sensor and a second saturation pressure for the second sensor. The function for the method comprises a corrective value based on a ratio between the first saturation value and the second saturation value. Compensating the first sensor may include the steps of producing a corrected relative humidity value for the first sensor, where the corrected relative humidity value comprises a product of the first relative humidity and the corrective value.

In another exemplary embodiment, the first relative humidity at a first temperature is determined along multiple points of a time base, and the second temperature is determined along the multiple points of the time base. A time-based filter may be applied for the multiple points of the time base. The time-based filter may be applied sequentially or symmetrically for the multiple points of the time base.

BRIEF DESCRIPTION OF THE DRAWINGS

The present invention is illustrated by way of example and not limitation in the figures of the accompanying drawings, in which like references indicate similar elements and in which.

DETAILED DESCRIPTION

Humidity sensors or hygrometers are instruments used for measuring the moisture content in the atmosphere. Typically, humidity sensors rely on measurements of some other quantity such as temperature, pressure, mass or a mechanical or electrical change in a substance as moisture is absorbed. Using calibration, calculation and processing, these measured quantities can lead to a measurement of humidity. A temperature of condensation, or dew point, or changes in electrical capacitance or resistance may be used to measure humidity differences. For capacitive humidity sensors, the effect of humidity on a dielectric constant of a polymer or metal oxide material is measured. For resistive humidity sensors, the change in electrical resistance of a material due to humidity is measured. Typical materials may include salts and conductive polymers. For resistive sensors, the material properties may to depend both on humidity and temperature, which means that the sensor may be combined with a temperature sensor. In other sensors, such as thermal conductivity humidity sensors, the change in thermal conductivity of air due to humidity is measured. These sensors may measure absolute humidity rather than relative humidity. Still other sensors include psychrometers, which may include a dry thermometer and a wet thermometer, which may be kept moist with water on a sock or wick. These thermometers are sometimes referred to as a dry-bulb and a wet-bulb, respectively. At temperatures above the freezing point of water, evaporation of water from the wick lowers the temperature, so that the wet-bulb thermometer may show a lower temperature than that of the dry-bulb thermometer. Relative humidity may be computed from the ambient temperature determined in the dry-bulb thermometer and the difference in temperatures as determined in the wet-bulb and dry-bulb thermometers. Relative humidity can also be determined by processing and locating the intersection of the wet and dry-bulb temperatures on a psychrometric table, chart or scale via microcontroller. The two thermometers coincide when the air is fully saturated, and the greater the difference, the drier the air.

Figure 1:
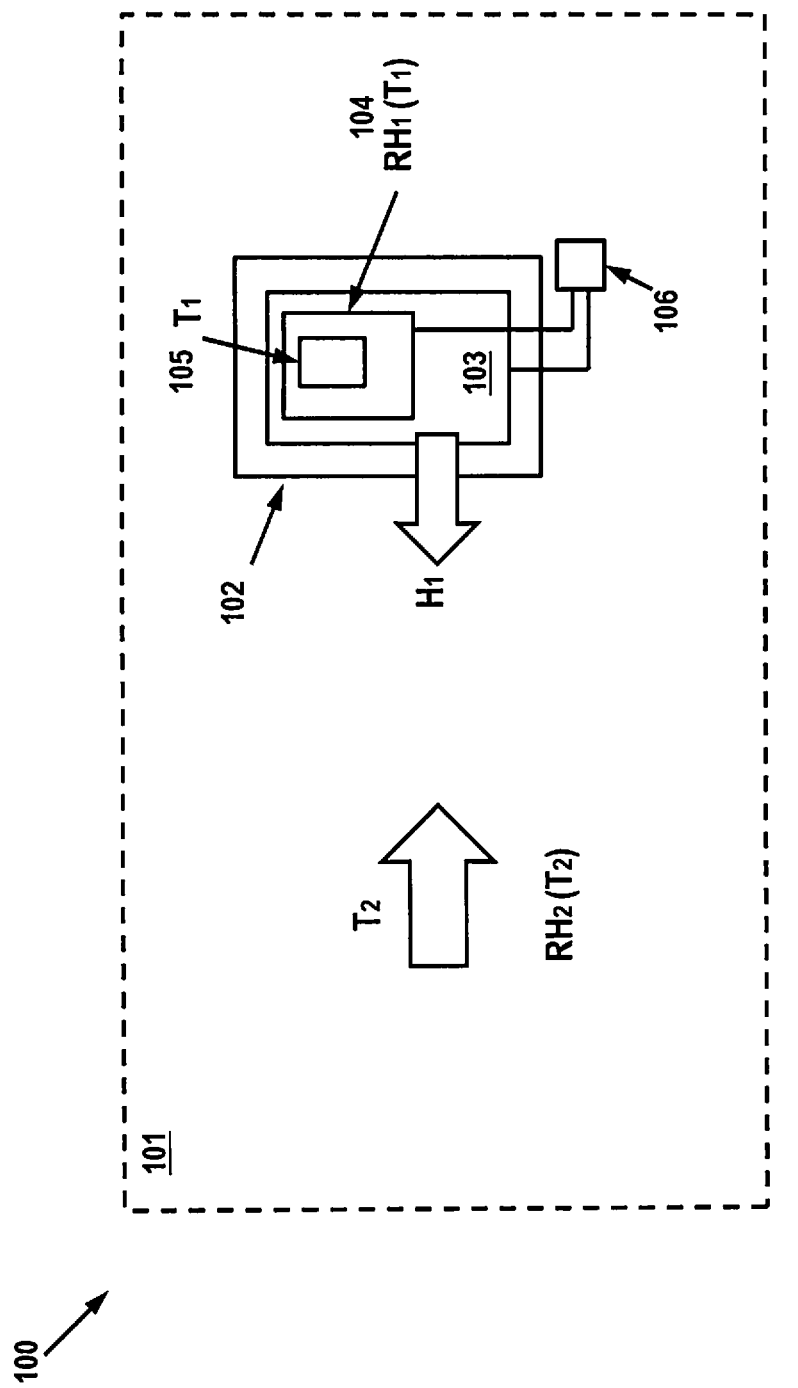
FIG. 1 illustrates an exemplary embodiment of a temperature-compensated humidity sensor, which is configured to account for ambient area temperatures and internal temperatures.

Regardless of the type of humidity sensor being used, the present disclosure is directed to any humidity sensor utilizing a temperature component. Turning to FIG. 1, an exemplary embodiment is disclosed where a sensor 102 is positioned in a zone 101, which may be a room, enclosure, or other area. Sensor 102 comprises a case which may include wall mounts, electronic circuitry 103, and sensor circuitry 104 comprising an internal sensor/thermistor 105. Sensor 102 advantageously comprises a second sensor/thermistor 106, which may be coupled to electronic and sensor circuitry (103, 104) utilizing a thermocouple or any other suitable means. It should be understood by those skilled in the art that, while circuitry 103, 104 and sensor/thermistor 105 are depicted as separate blocks in FIG. 1, the circuitry and sensors may be integrated into one circuit, circuit board or substrate, or may alternately be separated into multiple different components, depending on the needs of the electronic designer.

Sensor circuitry 104 may comprise an internal humidity sensor and an associated temperature sensor (105) that is configured to measure a local temperature, which, in this embodiment, includes the temperature in the wall mount case. Under normal operating conditions, the internal temperature ($T_1$) of the case is elevated by the internal electronics, which can introduce error in the humidity sensor with respect to room humidity (RH). Accordingly, under one embodiment, a second temperature sensor 106 is extended through the wall mount case enclosure 102 such that it can accurately measure the room temperature. The thermocouples for sensor/thermistor 106 are preferably small and should require two wires for operation, so they can easily be positioned under an edge of wall mount case 102 and not be easily visible. Alternately, the thermocouples may be covered by a secondary encasement to protect and hide the wires from sight.

In the embodiment of FIG. 1 the second (external) temperature sensor 106 may be used to compensate for potential inaccuracies in sensor measurements within enclosure 102. Under one illustrative example, the sensor arrangement is configured to measure relative humidity, which may be defined generally as a ratio of the actual amount of water vapor present in a volume of air at a given temperature to the maximum amount that the air could hold at that temperature, expressed as a percentage. Since warm air can hold more water vapor than cool air, a particular amount of water vapor will yield a lower relative humidity in warm air than it does in cool air. As can be seen in the figure, sensor 102 needs to take into consideration and compensate relative humidity ($RH_1$) at temperature ($T_1$) for the area 102, to measure relative humidity ($RH_2$) at temperature ($T_2$) for area 101 surrounding sensor 102. Relative humidity for sensor 102 may be determined by $$RH(T_1) = P_p / P(T_1)_{sat}$$

where $RH(T_1)$=the relative humidity and temperature ($T_1$);
$P_p$=the partial pressure of water in the air; and
$P(T_1)_{sat}$=the saturation pressure of water at temperature $T_1$.

From this proportionality, the relationship to the relative humidity and temperature of the room ($RH(T_1)$) can be expressed as:

$$RH(T_1) * (P(T_1)_{sat} / P(T_2)_{sat}) = RH(T_2)$$

where $P(T)_{sat}$ is only a function of temperature. Accordingly, the relative humidity and temperature of area 101 may be accurately determined by taking the relative humidity and temperature ($RH(T_1)$), determined by sensor 104, and making it a product of a ratio between the saturation pressure of water at temperature $T_1$, determined by sensor 104, and the saturation pressure of water at temperature $T_2$, determined by sensor 106 $P(T_1)_{sat}/P(T_2)_{sat}$. With regard to the saturation pressure of water vapor in FIG. 1, this can be expressed as:

$$P(T)_{sat} = e^{(77.3450 + 0.0057T - 7235/T)} / T8.2$$

where:

$P(T)_{sat}$=water vapor saturation pressure (Pa) at temperature T(K);
e=constant 2.71828; and
T=dry bulb temperature of the moist air (K).

This embodiment described above advantageously compensates humidity particularly for stagnant environments, even if the internal heat is changing due to changes in the operation of the electronic components (current loops, etc.). However, air flow in most areas (such as office spaces) is dynamic, with fans and other air moving systems changing the airflow at arbitrary times. If air stream(s) of different temperatures pass over the wall mount case, the external sensor/thermistor ( ) 106 will react much faster than the internal humidity sensor ($T_1$) in the wall mount case. This dynamic change could cause and extreme error in humidity, causing other elements of the system to erroneously engage.

Figure 2:
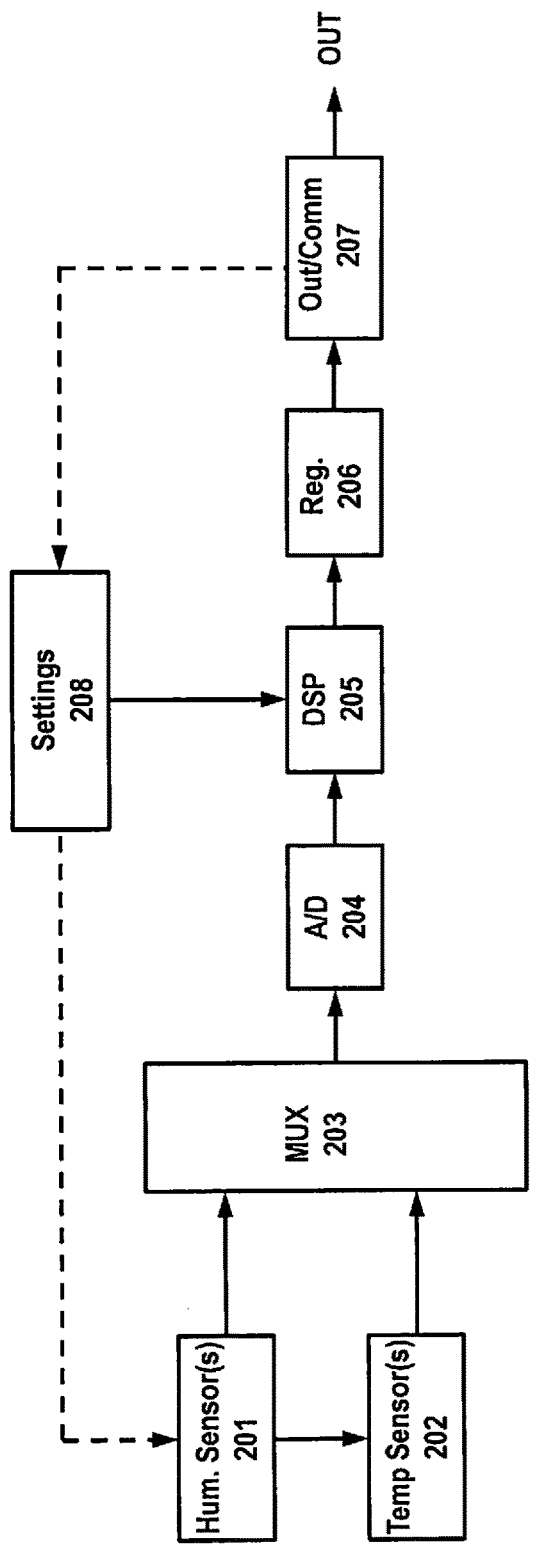
FIG. 2 is an exemplary embodiment illustrating a processing and communications configuration for the sensor of FIG. 1.

In order to compensate for such errors, further processing may be required for the sensor signals. Turning to FIG. 2, an exemplary sensor block diagram configuration is shown, comprising inputs from one or more humidity sensors 201 and temperature sensors 202. The dual-sensor configuration of FIG. 1 may be combined in the embodiment of FIG. 2, or may have separate circuitry to accommodate the readings of each sensor ($RH(T_1)$, $RH(T_2)$). The signals from humidity sensors 201 and temperature sensors 202 may be multiplexed and transmitted to analog-to-digital (A/D) converter 204 for digital conversion, and processed in digital signal processor (DSP) 205. DSP 205 may comprise a universal or dedicated processor responsible for all sensor processing. Alternately, DSP 205 may comprise one or more processors in communication with a central processing unit. The DSP and sensor settings may be controlled and/or calibrated by settings module 208, which may comprises a non-volatile memory, such as EEPROM. Outputs from DSP 205 may be stored in register 206, and forwarded to output/communication module 207.

Module 207 is configured to communicate sensor outputs (OUT) to other devices or peripherals that may be in communication with the sensor. In one embodiment, module 207 comprises a Serial Peripheral Interface, which is a synchronous serial data link capable of operating in full duplex mode. In this embodiment, sensors may communicate with other sensors or devices in master/slave mode, where the master device may initiate a data frame. Multiple slave devices may be allowed with individual slave select lines. In another embodiment, module 207 comprises a Modbus interface that allows the sensor to communicate data packets between many devices using the EIA-232 or EIE-285 protocols. The protocol defines function codes and the encoding scheme for transferring data as either single points (1-bit, coils) or as 16-bit data registers. This basic data packet is then encapsulated according to the protocol specifications for Modbus ASCII, RTU, or TCP. In another exemplary embodiment, module 207 comprises a BACnet interface, or "Building Automation and Control net," which is an Ethernet based, ASHRAE (American Society for Heating, Refrigeration and Air-Conditioning Engineers) standard. This protocol defines data communication services for sensor and equipment which is used for monitoring and control of heating, ventilation, air conditioning and refrigeration (HVAC&R). BACnet provides comprehensive sets of messages for conveying encoded binary, analog and alphanumeric data between devices. It should be understood by those skilled in the art that other communication protocols may be used as well, depending on the application needs. In one embodiment of FIG. 2, output from module 207 may also be fed back they settings module 208 to adjust or calibrate operation of DSP 205, and/or sensors 201-202.

Utilizing the configuration of FIG. 2, temperature differences due to air flow in an area discussed above may be corrected using a time-based filter algorithm for sensor readings. An exemplary moving average filter operates by averaging a number of points from the sensor input signal to produce each point in an output signal. This may be expressed algorithmically as $$y(i) = \frac{1}{M} \sum_{j=0}^{M-1} x(i+j)$$

where x( ) is a sensor input signal, y( ) is an output signal and M is the number of points in the average. Thus, as an example, in a 5 point moving average filter, a sensor signal point 10 in the output signal is given by $$y(10) = \frac{x(10) + x(11) + x(12) + x(13) + x(14)}{5}$$

Alternately, the group of points from the input signal may be chosen symmetrically around the output point, resulting in $$y(i) = \frac{1}{M} \sum_{j=-(M-1)/2}^{(M-1)/2} x(i+j), \text{ or}$$

$$y(10) = \frac{x(8) + x(9) + x(10) + x(11) + x(12)}{5}$$

Accordingly, a time base filter (or "rolling average") can be assigned to the values of the external sensor/thermistor 106 ($T_2$) to effectively slow down the reaction time to align with the internal humidity sensor 105 ($T_1$).

In another embodiment, the temperature difference between the two sensors (105, 106) may be limited as a boundary condition to the maximum difference between startup and maximum temperature difference in stagnant air. This can be determined by recording the temperature difference between $T_1$ and $T_2$ when the case and electronics are cooled to room temperature. After powering the electronics, the two temperatures are immediately recorded and used to adjust both resistors to room temperature. The electronics is then allowed to heat the internal humidity sensor and thermistor to a maximum temperature in stagnant air, wherein the temperatures are recorded again. This difference may be used for DSP 205 as a maximum temperature difference caused by the electronic heating alone, which may assist in compensating the sensors disclosed herein. Dynamic air currents in an area can cause much larger temperature differentials which are not related to internal electronic heating. Accordingly, they can be ignored as temperature difference outside of the determined limits. The rate of change of the time-based filter above can be adjusted for the difference between the two temperature sensors such that small temperature differences react faster than large differences.

Figure 3:
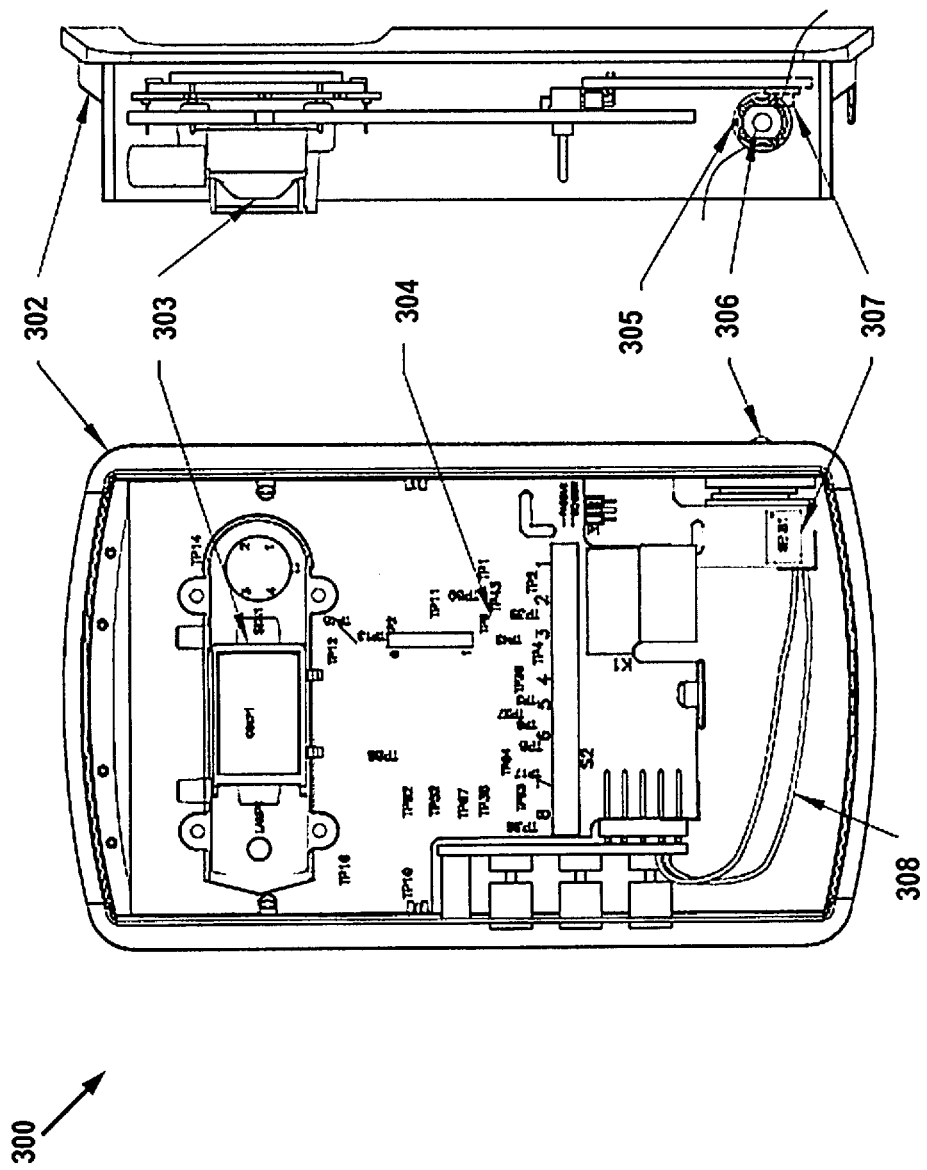
FIG. 3 is an exemplary schematic diagram for the sensor of FIG. 1, illustrating the arrangements of physical components for temperature and humidity sensing.

Turning now to FIG. 3, an exemplary schematic illustration is provided for the sensor configuration of FIG. 1. Here, wall mount case 302 in contained in an area or room zone (101) which creates a boundary for the ambient room temperature $T_2$ and room humidity $RH_2$ at $T_2$. Wall mount case 302 comprises a relative humidity sensor 307 with on-board temperature sensor 307, where both sensors may be at elevated internal box temperature $T_1$ as heated by thermal energy from electronic components 304 and CO2 sensor 303. A second temperature sensor 306 is extended out of a hole 305 in the wall mount case 302 to measure ambient temperature $T_2$ and may be further isolated from the case wall by a thermistor mounting insert 305 with 3 fingers to minimize thermal conduction from case 302. Wires 308 connect sensor 306 to the electronics board 304.

Figure 4:
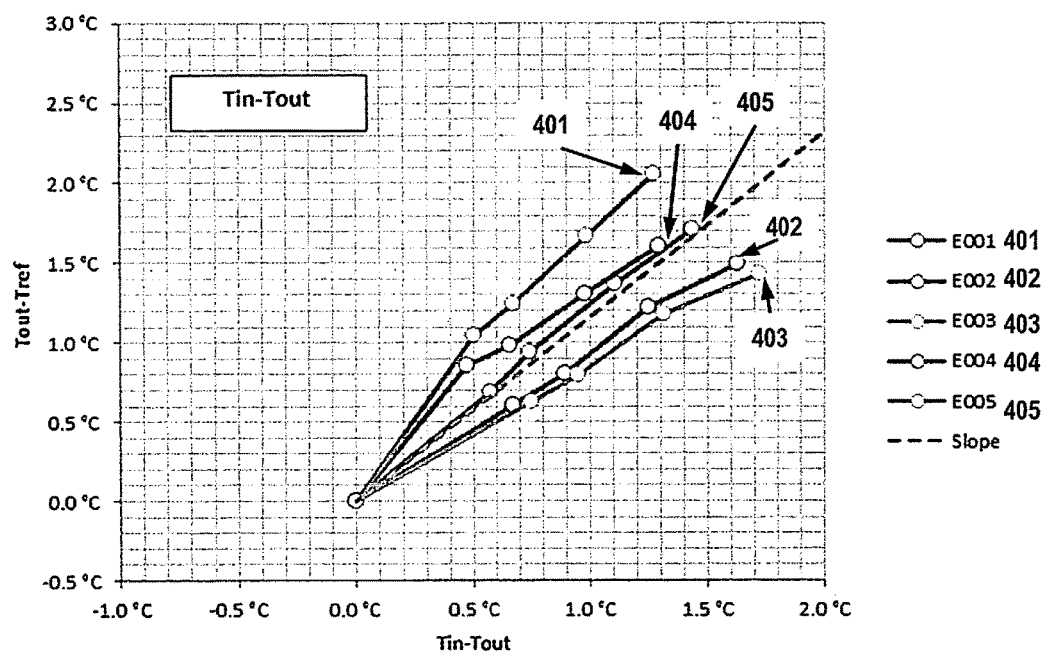
FIG. 4 is an exemplary graph illustrating compensation of the sensors reference (room) temperature.

In certain embodiments, temperature sensor 306 may be elevated above room temp by wall temperature 302. In this case, temperate sensors 307 and 306 can be used to estimate room temperature 01. The compensated temperature from 306 and 307 may then be used to determine the saturation pressure of room 101 and compensate internal humidity 104 to room humidity 101. Temperature sensors 306 and 307 can be calibrated to room temperature on startup of sensor 102 before internal heating occurs. FIG. 4 provides an exemplary graph illustrating compensation of sensors to a reference (room) temperature. Here, the sensors are normalized to each other and to room temperature, where the slope (dotted line) may be used to compensate $T_{out}$ to room temp ($T_{ref}$) very accurately. Lines 401 to 405 represent temperature measurements between the difference in the two sensors and the difference between the $T_{out}$ and room temperature ($T_{ref}$). This slope is determined experimentally for several sensors and the slope of the best fit line through the test sensors is used for all production sensors using this configuration. The estimated room temperature is determined by the established slope: m=$(T_{out}-T_{ref})/(T_{in}-T_{out})$. Next, Tin and Tout are measured, and room temperature is determined by:

$$T_{room} = T_{out} - (m*(T_{in}-T_{out}))$$

Thus, for example for m=1.1333 from the graph, if $T_{in}-T_{out}=1C$ and $T_{out}=20C$, $T_{room}=20C-1.1333*1C=18.86C$ The $T_{room}$ estimate may then be used to compensate RH sensor to high accuracy. Such a configuration may effectively compensate for RH, as the percentage of RH measurements is greatly affected by temperature as RH increases. For example a 0.5 C error in temp would normally cause 2% error in RH at 60% RH. The compensated temperature may further be used to compensate relative humidity ($RH_1$) 104 to the relative humidity (RH) of room 101.

While at least one example embodiment has been presented in the foregoing detailed description, it should be appreciated that a vast number of variations exist. It should also be appreciated that the example embodiment or embodiments described herein are not intended to limit the scope, applicability, or configuration of the invention in any way. Rather, the foregoing detailed description will provide those skilled in the art with a convenient and edifying road map for implementing the described embodiment or embodiments. It should be understood that various changes can be made in the function and arrangement of elements without departing from the scope of the invention and the legal equivalents thereof.

What is claimed is:

1. An apparatus for determining relative humidity, comprising:
   a housing;
   a relative humidity sensor arranged internal to the housing and configured to measure relative humidity internal to the housing;
   a first temperature sensor mounted on an interior of the housing, wherein the first temperature sensor is configured to measure a temperature internal to the housing;
   a second temperature sensor mounted on an exterior of the housing, wherein the second temperature sensor is configured to measure a temperature external to the housing; and
   a processor, operatively coupled to the humidity sensor, the first temperature sensor, and the second temperature sensor;
   wherein the processor is configured to obtain from the first temperature sensor the temperature measured internal to the housing, obtain from the second temperature sensor the temperature measured external to the housing, and obtain from the relative humidity sensor the relative humidity measured internal to the housing;
   wherein the processor is configured to calculate a compensated temperature external to the housing as a function of the temperature measured external to the housing, the compensated temperature external to the housing accounting for heating of the second temperature sensor resulting from heat transfer from internal to the housing to the exterior of the housing where the second temperature sensor is mounted; and
   wherein the processor is further configured to calculate the relative humidity external to the housing as a function of the temperature measured internal to the housing, the compensated temperature external to the housing, and the relative humidity measured internal to the housing.

2. The apparatus recited in claim 1, wherein the processor is configured to calculate the compensated temperature external to the housing according to:

$$T_{room} = T_{out} - (m*(T_{in} - T_{out}))$$

where $T_{room}$ is the compensated temperature external to the housing, $T_{out}$ is the temperature measured external to the housing, $T_{in}$ is the temperature measured internal to the housing, and m is a value that correlates the effect that the temperature measured internal to the housing has on the temperature the temperature measured external to the housing due to heat transfer through the housing where the second temperature sensor is mounted.

3. The apparatus recited in claim 2, wherein m is determined experimentally by:
   placing a plurality of sample apparatuses in an area;
   normalizing the first and second temperature sensors of the plurality of sample apparatuses to each other and to an ambient temperature in the area;
   supplying power to the plurality of sample apparatuses;
   recording multiple temperature pairs comprising the temperatures measured internal and external to the housing of each sample apparatus at different time intervals;
   plotting, for each temperature pair of each sample apparatus, values related to the difference between the temperatures measured internal and external to the housing versus the difference between the temperature measured external to the housing and the ambient temperature;
   determining a best fit line for the plotted values; and
   determining m as the slope of the best fit line.

4. The apparatus recited in claim 1, wherein the processor is configured to apply a time-based filter to calculate a moving average of the temperatures measured external to the housing, the processor being further configured to calculate the compensated temperature external to the housing as a function of the moving average of the temperatures measured external to the housing.

5. The apparatus recited in claim 4, wherein the processor is configured to apply the time-based filter sequentially.

6. The apparatus recited in claim 4, wherein the processor is configured to apply the time-based filter symmetrically.

7. A method for determining relative humidity with a sensor including a housing, a relative humidity sensor arranged internal to the housing, a first temperature sensor mounted on an interior of the housing, and a second temperature sensor mounted on an exterior of the housing, the method comprising:
   measuring via the relative humidity sensor a relative humidity internal to the housing;
   measuring via the first temperature sensor a temperature internal to the housing;
   measuring via the second temperature sensor a temperature external to the housing;
   calculating a compensated temperature external to the housing as a function of the temperature measured external to the housing, the compensated temperature external to the housing accounting for heating of the second temperature sensor resulting from heat transfer from internal to the housing to the exterior of the housing where the second temperature sensor is mounted; and
   calculating the relative humidity external to the housing as a function of the temperature measured internal to the housing, the compensated temperature external to the housing, and the relative humidity measured internal to the housing.

8. The method recited in claim 7, wherein calculating the compensated temperature external to the housing comprises calculating the compensated temperature external to the housing according to:

$$T_{room} = T_{out} - (m*(T_{in} - T_{out}))$$

where $T_{room}$ is the compensated temperature external to the housing, $T_{out}$ is the temperature measured external to the housing, $T_{in}$ is the temperature measured internal to the housing, and m is a value that correlates the effect that the temperature measured internal to the housing has on the temperature the temperature measured external to the housing due to heat transfer through the housing where the second temperature sensor is mounted.

9. The method recited in claim 8, further comprising determining m experimentally by:
placing a plurality of sample apparatuses in an area;
normalizing the first and second temperature sensors of the plurality of sample apparatuses to each other and to an ambient temperature in the area;
supplying power to the plurality of sample apparatuses;
recording multiple temperature pairs comprising the temperatures measured internal and external to the housing of each sample apparatus at different time intervals;
plotting, for each temperature pair of each sample apparatus, values related to the difference between the temperatures measured internal and external to the housing versus the difference between the temperature measured external to the housing and the ambient temperature;
determining a best fit line for the plotted values; and
determining m as the slope of the best fit line.

10. The method recited in claim 9, further comprising applying a time-based filter to calculate a moving average of the temperatures measured external to the housing, wherein calculating the compensated temperature external to the housing comprises calculating he compensated temperature external to the housing as a function of the moving average of the temperatures measured external to the housing.

11. The method recited in claim 10, further comprising applying the time-based filter sequentially.

12. The method recited in claim 10, further comprising applying the time-based filter symmetrically.

13. A method for determining relative humidity with a relative humidity sensor comprising:
compensating a temperature measured external to a sensor housing via an externally mounted temperature sensor for heating of the externally mounted temperature sensor due to heat generated by electronic components of the relative humidity sensor internal to the housing; and
calculating the relative humidity external to the housing as a function of a temperature measured internal to the housing, the compensated temperature external to the housing, and a relative humidity measured internal to the housing.

14. The method recited in claim 13, wherein calculating the compensated temperature external to the housing comprises calculating the compensated temperature external to the housing according to:

$$T_{room} = T_{out} - (m*(T_{in} - T_{out}))$$

where $T_{room}$ is the compensated temperature external to the housing, $T_{out}$ is the temperature measured external to the housing, $T_{in}$ is the temperature measured internal to the housing, and m is a value that correlates the effect that the temperature measured internal to the housing has on the temperature the temperature measured external to the housing due to the heat generated by electronic components of the relative humidity sensor internal to the housing.

* * * * *